United States Patent [19]

Hidaka et al.

[11] 4,421,754
[45] Dec. 20, 1983

[54] SYNDONIMINE DERIVATIVES, PROCESS FOR PRODUCTION THEREOF, AND USE THEREOF

[75] Inventors: Hiroyoshi Hidaka, 766-38, Kannonji-cho, Tsu-shi, Mie-ken, Japan; Ikuo Matsumoto, Tokyo, Japan; Junji Yoshizawa, Machida, Japan; Shigenori Kotani, Kodaira, Japan

[73] Assignee: Hiroyoshi Hidaka, Mie, Japan

[21] Appl. No.: 402,974

[22] Filed: Jul. 29, 1982

[30] Foreign Application Priority Data

Aug. 24, 1981 [JP]  Japan ................... 56-131564

[51] Int. Cl.³ ................. C07D 413/04; A61K 31/495
[52] U.S. Cl. .................... 424/250; 544/367; 544/382; 548/125
[58] Field of Search ................ 544/367; 424/250

[56] References Cited

U.S. PATENT DOCUMENTS

| | | | |
|---|---|---|---|
| 3,812,128 | 5/1974 | Masuda | 544/367 |
| 3,833,589 | 9/1974 | Simpson | 544/367 |

FOREIGN PATENT DOCUMENTS

| | | | |
|---|---|---|---|
| 44-18302 | 8/1969 | Japan | 544/367 |
| 46-6053 | 2/1971 | Japan | 544/367 |
| 48-32890 | 5/1973 | Japan | 544/367 |
| 1358413 | 7/1974 | United Kingdom | 544/367 |

OTHER PUBLICATIONS

Chem. Pharm. Bull. 18 (1) 128-132, (1970) "Studies on Mesoionic Compounds, I, Synthesis of 3-Dialkylaminosydnonimines" Masuda, et al.
Oyo Yakuri (Applied Pharmacology) 2 (3) 280-287, (1968) "The Synthesis of Mesoionic and Related Compounds", Masuda et al.

*Primary Examiner*—Mark L. Berch
*Assistant Examiner*—S. A. Gibson
*Attorney, Agent, or Firm*—Sherman & Shalloway

[57] ABSTRACT

A 3-[4-(benzoylalkyl)piperazin-1-yl]sydnonimine compound represented by the following formula

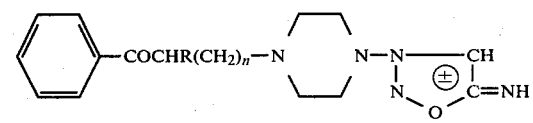

wherein R represents a hydrogen atom or an alkyl group having 1 to 8 carbon atoms, and n represents zero or an integer of 1 to 10, and its acid addition salt. The above sydnonimine compounds are useful for the treatment of troubles of the circulatory system and can be produced by contacting a 4-(benzoylalkyl)-1-(N-nitrosocyanomethylamino)piperazine represented by the following formula

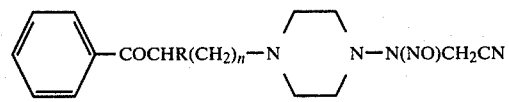

wherein R and n are as defined, with an acid.

8 Claims, No Drawings

SYNDONIMINE DERIVATIVES, PROCESS FOR PRODUCTION THEREOF, AND USE THEREOF

This invention relates to a novel sydnonimine derivative useful for the treatment of troubles of the circulatory system, a process for its production, and a pharmaceutical composition for the treatment of the aforesaid troubles.

More specifically, this invention relates to 3-[4-(benzoylalkyl)piperazin-1-yl]sydnonimine compounds of the following general formula (1)

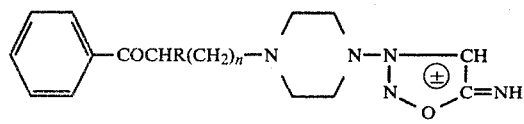

wherein R represents a hydrogen atom or an alkyl group having 1 to 8 carbon atoms, and n represents 0 or an integer of from 1 to 10,
and their acid addition salts. This invention also pertains to a process for the production of the compounds of formula (1) and their acid addition salts, and to a pharmaceutical composition comprising an amount, effective for the treatment of troubles of the circulatory system, of a compound of formula (1) or its acid addition salt and a pharmaceutically acceptable diluent or carrier.

Compounds of the following formula

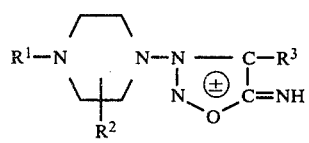

wherein $R^1$ represents an alkyl group, an aralkyl group, an aryl group, a 5-imino-3-sydnonyl group, or a group of the formula

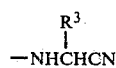

$R^2$ represents a hydrogen atom or an aryl group, and $R^3$ represents a hydrogen atom or an alkyl group,
have previously been known, and it has also been known that these compounds are useful as medicines which exhibit unique pharmacological activities on the circulatory system and the central nervous system (Japanese Patent Publication No. 18302/1969).

We have been engaged in developing new piperazinosydnonimine derivatives, and finally succeeded in synthesizing the piperazinosydnonimine compounds having a benzoyl alkyl group as represented by the above formula (1) and their acid addition salts which have not been described previously in the literature. We have also found that the compounds of formula (1) and their acid addition salts exhibit an inhibiting activity on platelet aggregation and a relaxing activity on vascular walls, and are useful for the prevention and treatment of various troubles of the circulatory system as peripheral circulation improvers, coronary artery dilators, cerebral thrombosis treating agents, etc.

It is an object of this invention therefore to provide novel piperazinosydnonimine compounds of formula (1) and their acid addition salts.

Another object of this invention is to provide a process for the production of the compounds of formula (1) and their acid addition salts.

Still another object of this invention is to provide a pharmaceutical composition comprising a compound of formula (1) or its pharmaceutically acceptable acid addition salt as an active ingredient.

The above and other objects and advantages of this invention will become more apparent from the following description.

In the compounds of this invention represented by formula (1), $C_1$-$C_8$ alkyl group for R may be a linear or branched alkyl group such as methyl, ethyl, propyl, isopropyl, butyl, sec-butyl, tert-butyl and pentyl. In formula (1), n represents zero or an integer of from 1 to 10, preferably zero or an integer of from 1 to 7.

The acid addition salts of the compounds of formula (1) are preferably pharmaceutically acceptable acid addition salts. For example, they are salts with inorganic acids such as hydrochloric acid, nitric acid, sulfuric acid and phosphoric acid, and salts with organic acids such as formic acid, acetic acid, propionic acid, alkylsulfonic acids and arylsulfonic acids. The hydrochlorides are especially preferred.

Examples of preferred compounds of formula (1) and their acid addition salts are as follows:

3-[4-(4-Benzoylbutyl)piperazin-1-yl]sydnonimine and its dihydrochloride (compound A), 3-[4-(benzoylmethyl)piperazin-1-yl]sydnonimine and its dihydrochloride (compound B), 3-[4-(3-benzoylpropyl)piperazin-1-yl]sydnonimine and its dihydrochloride (compound C), 3-[4-(5-benzoylpentyl)piperazin-1-yl]sydnonimine and its dihydrochloride (compound D), 3-[4-(6-benzoylhexyl)piperazin-1-yl]sydnonimine and its dihydrochloride (compound E), 3-[4-(8-benzoyloctyl)piperazin-1-yl]sydnonimine and its dihydrochloride (compound F), and 3-[4-(4-benzoyl-6-methylheptyl)piperazin-1-yl]-sydnonimine and its dihydrochloride (compound G).

The compounds of formula (1) and their acid addition salts can be produced easily by contacting a 4-(benzoylalkyl)-1-(N-nitrosocyanomethylamino)piperazine of the following formula (2)

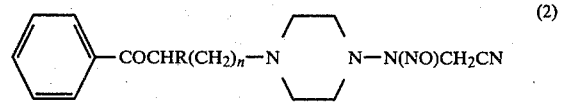

wherein R represents a hydrogen atom or an alkyl group having 1 to 8 carbon atoms, and n represents zero or an integer of from 1 to 10,
with an acid to induce cyclization reaction.

The compound of formula (2) has neither been described previously in the literature. It can be easily produced, for example, by introducing a nitroso group into a 4-(benzoylalkyl)-1-(cyanomethylamino)piperazine of the following formula (3)

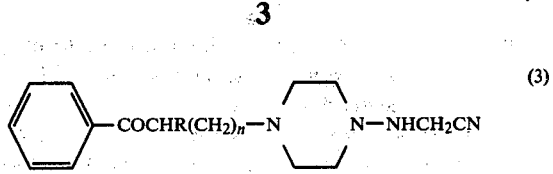

wherein R and n are as defined with regard to formula (1).

The compound of formula (3) can be produced easily from a benzoylalkyl halide, for example. The synthetic route of the compound of this invention including steps of forming the starting compounds can be schematically shown as follows.

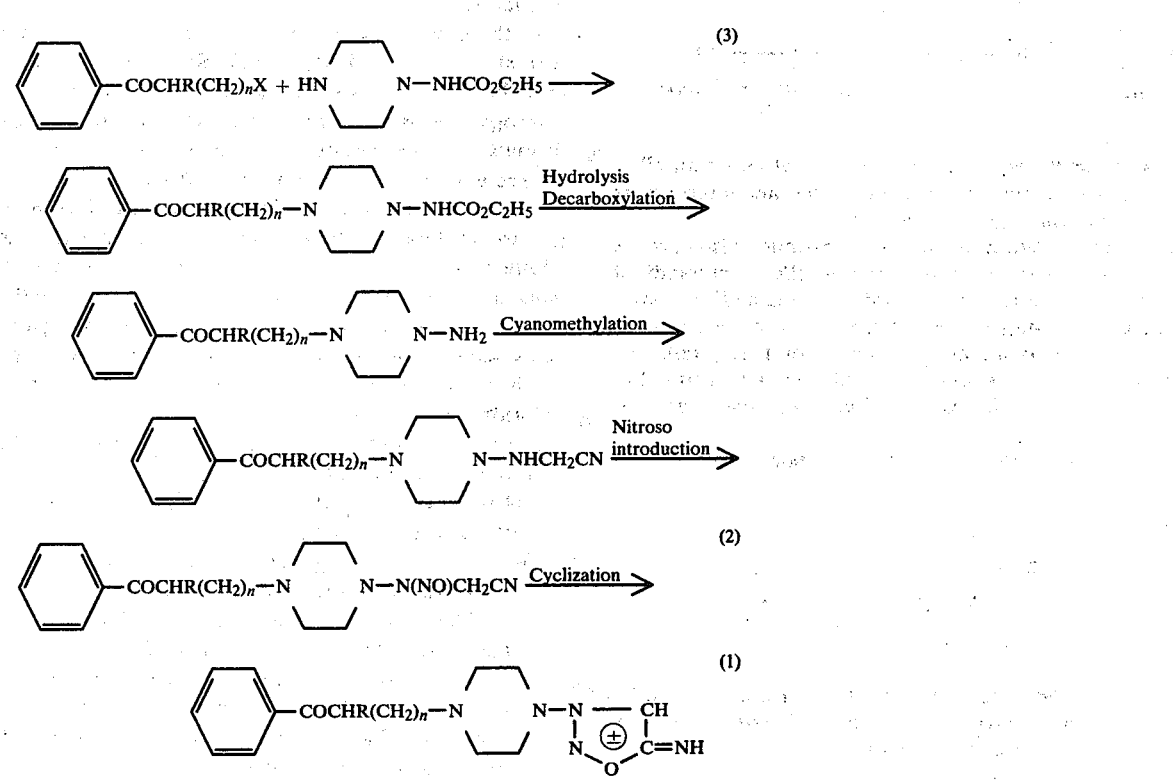

In the above formulae, X represents a halogen atom such as chlorine or bromine, and R and n are as defined with regard to formula (1).

The compound of formula (3) can be produced, for example, by the following method.

A benzoylalkyl halide is reacted with 1-(ethoxycarbonylamino)piperazine in the presence of an excessive amount of an alkali bicarbonate to give a 4-(benzoylalkyl)-1-(ethoxycarbonylamino)piperazine. This reaction is carried out under heat in an alcohol solvent such as methanol, ethanol, isopropanol or butanol. The reaction product is isolated by solvent extraction. If desired, it may be purified by recrystallization. The resulting 4-(benzoylalkyl)-1-(ethoxycarbonylamino)-piperazine is heated together with a soluble alkali such as potassium hydroxide or sodium hydroxide, whereby hydrolysis and subsequently decarboxylation take place to yield a 4-(benzoylalkyl)-aminopiperazine. This hydrolysis and decarboxylation reaction is carried out in an alcohol solvent such as ethanol or methanol or a hydrous alcohol solvent such as hydrous ethanol or methanol at the boiling point of the solvent. The resulting 4-substituted-1-aminopiperzine can be isolated by solvent extraction. Usually, it is advantageous to use the reaction mixture directly in the subsequent step. The resulting 4-substituted-1-minopiperazine solution is then neutralized by adding an equivalent of hydrochloric acid, and reacted first with formaldehyde sodium bisulfite hydrate and then with potassium cyanide to produce a cyanomethylaminopiperazine derivative. This cyanomethylation reaction is carried out at a temperature of 50° to 70° C. The cyanomethylation product is isolated by extraction with an organic solvent, and if required, purified by recrystallization. The cyanomethylated derivative may be converted to its dihydrochloride by introducing hydrogen chloride into an ethanolic solution of it.

According to the process of this invention, the novel intermediate of formula (2) can be produced by introducing a nitroso group into the compound of formula (3) which can be obtained as shown above. This reaction can be carried out by utilizing known methods of nitrososation. For example, it can be effected by reacting the dihydrochloride of the compound of formula (3) with an alkali nitrite such as sodium nitrite or potassium nitrite at a relatively low temperature. The reaction can be performed by contacting the dihydrochloride of the compound of formula (3) with the alkali nitrite in an aqueous medium at a relatively low temperature of, for example, about −5° C. to about 10° C. The reaction proceeds rapidly, and ends in 0.5 to 5 hours. The reaction product is isolated from the reaction mixture by solvent extraction. Without particularly purifying it, the product is used in the subsequent cyclization step. As required, however, it may be purified by recrystallization, etc.

By contacting the compound of formula (2) with an acid in the presence of a solvent, the compound of formula (1) is obtained in the form of its acid addition salt. Any inorganic or organic acid can be used in this cyclization reaction. Preferably, acids capable of forming pharmaceutically acceptable acid addition salts are used. Examples of preferred acids include such inorganic acids as hydrochloric acid, nitric acid, sulfuric acid and phosphoric acid and such organic acids as formic acid, acetic acid, propionic acid, alkylsulfonic acids (e.g., methanesulfonic acid, ethanesulfonic acid and isethionic acid) and arylsulfonic acids (e.g., benzenesulfonic acid and p-toluenesulfonic acid).

Alcohols are preferred as the solvent used for the cyclization reaction, and lower alcohols such as methanol and ethanol may be cited as typical examples. The reaction is carried out preferably at relatively low temperature, for example about 0° C. to room temperature. Too high temperatures may result in undesirable side-reactions. The reaction time can be properly chosen, and may, for example, be about 5 to about 24 hours. The resulting acid addition salt may be isolated and purified from the reaction mixture as a solid, and purified by recrystallization.

The free compound of formula (1) can be obtained by, for example, neutralizing a methanol solution of the corresponding hydrochloride with an equivalent of sodium methoxide, removing the precipitated inorganic salt by filtration, and then distilling off the solvent under reduced pressure. Alternatively, it can be obtained by subjecting a methanol solution of the hydrochloride to dehydrochlorination with a basic ion exchange resin.

The compounds of formula (1) and their acid addition salts in accordance with this invention have very strong platelet aggregation inhibiting activity and vascular wall relaxing activity, and are therefore useful as treating agents for the prevention, therapy, etc. of troubles of the circulatory system, for example as peripheral circulation improvers, coronary artery dilators, cerebral thrombosis treating agents, etc.

Thus, according to this invention, there can be provided a pharmaceutical composition comprising an amount, effective for treating troubles of the circulatory system, of a 3-[4-(benzoylalkyl)piperazin-1-yl]sydnonimine compound of the following formula (1)

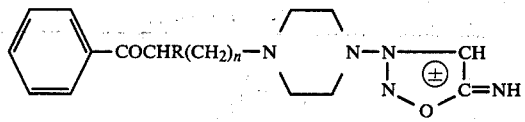

(1)

wherein R represents a hydrogen atom or an alkyl group having 1 to 8 carbon atoms and n represents zero or an integer of from 1 to 10,
or its pharmaceutically acceptable acid addition salt and a pharmaceutically acceptable diluent or carrier.

The pharmaceutical composition of this invention may be in various forms prepared by methods known in the pharmaceutical field. For example, it may be in the form of powders, granules, tablets, injections, capsules, etc. The pharmaceutically acceptable diluent or carrier used in the pharmaceutical composition of this invention may be any liquid or solid diluent or carrier known in pharmaceutical fields. Examples of such a liquid or solid diluent or carrier include distilled water, ethanol, isopropanol, propylene glycol, glycerol, lactose, corn starch, crystalline cellulose, talc, stearic acid, magnesium stearate, carboxymethyl cellulose, hydroxypropyl cellulose, gum arabic and beeswax.

The pharmaceutical composition of this invention may contain the compound of formula (1) in any amount which is effective for the treatment of troubles of the circulatory system. For example, its amount is 0.01 to 99% by weight based on the weight of the pharmaceutical composition. The dose of the compound of formula (1) in accordance with this invention may, for example, be about 0.1 to about 100 mg/body/day, preferably about 0.3 to about 30 mg/body/day. The toxicity of the compounds (1) of this invention is extremely low as shown by the results of a test described hereinbelow.

Preferred examples of the compounds of formula (1) are those in which R is a hydrogen atom or an isobutyl group, and their acid addition salts, especially their hydrochlorides. Compounds of formula (1) in which n is 0, 2, 3, 4, 5 or 7 and their acid addition salts are also preferred. An especially preferred compound is 3-[4-(4-benzoylbutyl)piperazin-1-yl]sydnonimine dihydrochloride (compound A).

Using the compound A as a typical example, the following pharmacological and toxicity tests were conducted.

I. Pharmacological tests (1) Activity on the extracted blood vessels of a rabbit A rabbit with a body weight of 2 to 3 kg was bled to death, and the thoracic aorta, mesenteric artery, renal artery, basilar artery and portal vein were extracted. Helical stripe specimens of these blood vessels were prepared. The specimens were suspended in a Magnus vessel, and the relaxing activity of the compound A against contraction of the specimens by KCl was examined. It was found that the $ED_{50}$ of the compound A was 4 $\mu M$ at the portal vein, 1.3 $\mu M$ at the basilar artery, 0.2 $\mu M$ at the coronary artery, mesenteric artery and thoracic aorta, and 0.1 $\mu M$ at the renal artery. It is seen therefore that the compound A differs in activity from nitroglycerin having a strong relaxing activity on the veins, and has a strong relaxing activity on arteries, for example the coronary artery, the renal artery, etc.

(2) Activity on human platelet

PRP (platelet-rich plasma) was centrifugally separated from human blood to which sodium citrate had been added, and used as a sample. Collagen, adrenaline and adenosine diphosphate were used as substances causing platelet aggregation. The inhibitory effect of the compound A against platelet aggregation included by these substances was examined. It was found that the concentration of the compound A which achieved a 50% inhibition of the platelet aggregation induced by these substances was 3.4 $\mu M$ for collagen, 1.5 $\mu M$ for adenosine diphosphate and 0.8 $\mu M$ for adrenaline.

It is seen from the results that the present compound is a strong inhibitor against the aggregation of human blood platelet. Furthermore, since the concentrations of the present compound which achieved a 50% inhibition differ only slightly among the aggregation-inducing substances, it is presumed that the present compound acts on a function common to all aggregation-inducing substances, for example on calcium metabolism.

(3) Activity on the respiration, blood pressure, heart rate and blood flow rate of a dog.

The test was carried out under pentobarbital anesthesia using a male Beagle dog having a body weight of about 10 kg. The respiration was measured by means of a pneumotachograph; the blood pressure, by inserting a cannula into the femoral artery; the heart rate, by a cardiotachometer; and the rate of blood flow, by means of an electromagnetic blood flow meter by mounting a measuring probe on the vertebral artery and the femoral artery.

The present compound A was intraveneously administered as a solution in physiological saline. No appreciable effect was seen when the present compound was administered in a dose of 10 μg/kg, but at a dose of 100 μg/kg, slight degrees of a fall in blood pressure and a decrease in the force of the pulse were noted. When it was administered in a dose of 500 μg/kg, a transient fall in blood pressure and a subsequent lasting fall in blood pressure were noted. The rate of blood flow tended to increase at the central part as compared with the peripheral part.

II. Acute toxicity test

An acute toxicity test was carried out by using male dd-strain mice (body weight 16 to 20 g). It was found that the $LD_{50}$ of the present compound A was 91 mg/kg in intravenous administration, 350 mg/kg in subcutaneous administration, and 750 mg/kg in oral administration.

III.

The inhibiting activity on human platelet aggregation and the relaxing activity on mesenteric artery (the artery being extracted from rabbits) of compounds B to G of the invention were also examined in the same way as in I, (1) and (2). The results are shown in Table 1 below. The mesenteric artery relaxing activity was shown in terms of the concentration (μM) of each compound which was required to cause 50% of the maximum relaxation, and the platelet aggregation inhibiting activity, in terms of the concentration (μM) of each compound which was required to inhibit aggregation to an extent of 50%. The platelet aggregation inhibiting activities of these compounds agreed relatively well with their artery relaxing activities

TABLE 1

| Compound | Mesenteric artery relaxing activity (μM) | Platelet aggregation inhibiting activity (μM) |
|---|---|---|
| B | 0.16 | 0.14 |
| C | 2.3 | 5.4 |
| D | 3.0 | 6.3 |
| E | 0.12 | 0.94 |
| F | 0.058 | 0.028 |
| G | 1.3 | 11.0 |

The production of the compounds of this invention and the starting compounds is illustrated by the following examples.

REFERENTIAL EXAMPLE 1

17.0 g of 1-benzoyl-4-bromobutane, 13.4 g of 1-(ethoxycarbonylamino)piperazine and 17.8 g of sodium hydrogen carbonate were heated under reflux in ethanol for 6 hours with stirring. The insoluble materials were removed from the reaction mixture by filtration. The solvent was distilled off, and water was added to the residue. The mixture was extracted with benzene. The extract was recrystallized from benzene-hexane to give 21.4 g of 4-(4-benzoylbutyl)-1-(ethoxycarbonylamino)-piperazine having a melting point of 105° to 106° C.

21.4 g of the resulting 4-(4-benzoylbutyl)-1-(ethoxycarbonylamino)piperazine was dissolved in 180 ml of ethanol, and a solution of 36.2 g of potassium hydroxide in 36 ml of water was added. The mixture was heated under reflux for 3 hours. The reaction mixture was cooled, and 136 ml of 4N hydrochloric acid was added to form a 4-(4-benzoylbutyl)-1-aminopiperazine solution.

To the 4-(4-benzoylbutyl)-1-aminopiperazine solution was added 11.7 g of formaldehyde sodium bisulfite hydrate, and the mixture was reacted at 60° C. for 2 hours. The reaction mixture was concentrated under reduced pressure to about half of its original amount, and reacted with 5.0 g of potassium cyanide at 60° C. for 3.5 hours. The reaction mixture was extracted with diethyl ether. The extract was dissolved in 200 ml of ethanol, and 16% HCl ethanol was added to adjust the pH of the solution to less than 1. There was precipitated 20.6 g of 4-(4-benzoylbutyl)-1-(cyanomethylamino)piperazine having a melting point of 176° C. (decomp.).

IR, $\nu_{max}^{KBr}$ (cm$^{-1}$): 3450–3350, 3160, 3030, 2950, 2640, 2500, 2450, 2050–2000, 1680, 1590, 1440, 1400, 1380, 1260, 1200, 1020, 980, 760, 735.

NMR (DMSO-d$_6$, 60 Mz) $\delta_{ppm}^{DMS}$: 8.12–7.85 (m, 2H), 7.70–7.45 (m, 3H), 4.09 (s, 2H), 3.83–2.78 (m, 10H), 3.08 (d, 2H), 1.86–1.48 (m, 4H).

REFERENTIAL EXAMPLE 2

By treating benzoyl alkyl halides as starting materials in the same way as in Referential Example 1, the 4-(benzoylalkyl)-1-(cyanomethylamino)piperazines shown in the following Table 2 were obtained.

TABLE 2

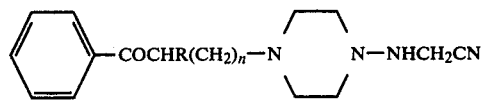

| R | n | Melting point (°C.) |
|---|---|---|
| H | 0 | 97–100 |
| H | 2 | 154–156 (decomp.) (dihydrochloride) |
| H | 4 | 164–165 (decomp.) (dihydrochloride) |
| H | 5 | 213–215 (decomp.) (dihydrochloride) |
| H | 7 | 48–49 |
| i-C$_4$H$_9$ | 3 | Oily product |

EXAMPLE 1

2.0 g of 4-(4-benzoylbutyl)-1-(cyanomethylamino)-piperazine dihydrochloride was dissolved in 22 ml of water, and while the solution was cooled to below 5° C., an aqueous solution containing 1.0 g of sodium nitrite was added over the course of 10 minutes. The reaction was carried out at this temperature for 2 hours. The reaction mixture was extracted with chloroform. The extract was washed with water and dried, and the chloroform was distilled off to give 4-(4-benzoylbutyl)-1-(N-nitrosocyanomethylamino)-piperazine.

The nitroso compound was dissolved in 10 ml of methanol, and 10 ml of 10% methanolic hydrochloric acid was added. The mixture was stored overnight at less than 5° C. The reaction mixture was then concentrated under reduced pressure, and the residue was recrystallized from methanol-ether to give 1.1 g (yield 48.6%) of 3-[4-(4-benzoylbutyl)-piperazine-1-yl]sydnonimine dihydrochloride having a melting point of 168° C. (decomp.).

| Elemental analysis for $C_{17}H_{25}N_5O_2Cl_2 \cdot \frac{1}{2}H_2O$ | | | | |
|---|---|---|---|---|
|  | C | H | N | Cl |
| Calculated (%): | 49.64 | 6.37 | 17.03 | 17.24 |
| Found (%): | 49.63 | 6.23 | 16.98 | 17.32 |

IR, $\nu_{max}^{KBr}(cm^{-1})$: 3420, 3200, 2950, 2650, 2540, 2450, 1670, 1595, 1440, 1380, 1210, 970, 960, 892, 762, 740, 700.

UV, $\lambda_{max}^{H2O}(nm)$: 247 ($\epsilon = 7320$), 291 ($\epsilon = 5070$).

NMR ($D_2C$, 60 Mz) $\delta_{ppm}^{DSS}$: 8.27 (s, 1H), 8.00–7.76 (m, 2H), 7.65–7.27 (m, 3H), 3.97–2.95 (m 10H), 2.65–2.83 (t, 2H), 1.96–1.65 (m, 4H).

EXAMPLE 2

A solution prepared by adding 10 ml of water and 19 ml of 1N hydrochloric acid to 1.6 g of 4-(benzoylmethyl)-1-(cyanomethylamino)piperazine was cooled to 4° to 5° C., and with stirring, 1.7 g of sodium nitrite was added. The mixture was reacted at 4° to 5° C. for 1.5 hours with stirring. The reaction mixture was extracted with chloroform. The extract was washed with water and dried, and chloroform was distilled off to give 4-(benzoylmethyl)-1-(N-nitrosocyanomethylamino)piperazine as a red oil.

The resulting 4-(benzoylmethyl)-1-(N-nitrosocyanomethylamino)piperazine was dissolved in 10 ml of methanol. In the solution was added 12 ml of 10% methanolic hydrochloric acid, and the mixture was reacted at 5° C. overnight. The reaction mixture was concentrated under reduced pressure, and the residue was recrystallized from methanol-ether to give 1.8 g (yield 81.8%) of 3-[4- (benzoylmethyl)piperazin-1-yl]sydnonimine dihydrochloride having a melting point of 182° to 184° C. (decomp.).

IR, $\nu_{max}^{Kbr}cm^{-1}$: 3350, 3050, 3000–2000, 1685, 1660, 1590, 1570, 1440, 1420, 1400, 1385, 1345, 1295, 1250, 1225, 1195, 1145, 1070, 1050.

NMR($D_2O$, 60 Mz)$\delta_{ppm}$: 8.38 (s, 1H), 8.1–7.8 (m, 2H), 7.8–7.5 (m, 3H), 5.22 (s, 2H), 4.4–3.6 (m, 8H).

EXAMPLES 3 TO 7

4-(Benzoylalkyl)-1-(cyanomethylamino)piperazines were reacted with sodium nitrite and then with methanolic hydrochloric acid in the same way as in Example 1 to give the following 3-[4-(benzoylalkyl)piperazin-1-yl]sydnonimine dihydrochlorides in yields of 60 to 80%.

3-[4-(3-Benzoylpropyl)piperazin-1-yl]sydnonimine dihydrochloride

Melting point: 176° C. (decomp.)

IR, $\nu_{max}^{KBr}cm^{-1}$: 3400, 3200–2300, 1680, 1595, 1575, 1460, 1440, 1410, 1385, 1360, 1290, 1215, 1180, 1100.

NMR($D_2O$, 60 Mz)$\delta_{ppm}$: 7.97 (s, 1H), 8.0–7.8 (m, 2H), 7.8–7.5 (m, 3H), 4.4–3.1 (m, 12H), 2.4–1.9 (m, 2H).

3-[4-(5-benzoylpentyl)piperazin-1-yl]sydnonimine dihydrochloride

Melting point: 173° C. (decomp.)

IR, $\nu_{max}^{KBr}cm^{-1}$: 3400, 3200–2300, 1675, 1595, 1580, 1470, 1450, 1380, 1305, 1270, 1250, 1200, 1175, 1145, 1100, 1080, 1030.

NMR($D_2O$, 60 Mz)$\delta_{ppm}$: 7.96 (s, 1H), 8.1–7.9 (m, 2H), 7.8–7.5 (m, 3H), 4.3–3.5 (m, 8H), 3.5–2.9 (m, 4H), 2.1–1.4 (m, 6H).

3-[4-(6-benzoylhexyl)piperazin-1-yl]sydnonimine dihydrochloride

Melting point: 164°–165° C. (decomp.)

IR, $\nu_{max}^{KBr}cm^{-1}$: 3350, 3200–2200, 1680, 1590, 1575, 1470, 1440, 1415, 1370, 1300, 1285, 1265, 1240, 1195, 1140, 1090, 1070, 1045.

NMR($D_2O$, 60 Mz)$\delta_{ppm}$: 7.95 (s, 1H), 8.1–7.85 (m, 2H), 7.8–7.5 (m, 3H), 4.4–3.5 (m, 10H), 3.4–2.8 (m, 2H), 2.1–1.3 (m, 8H).

3-[4-(8-benzoyloctyl)piperazin-1-yl]sydnonimine dihydrochloride

Melting point: 160°–162° C. (decomp.)

IR, $\nu_{max}^{KBr}cm^{-1}$: 3400, 3200–2300, 1700, 1675, 1590, 1570, 1460, 1440, 1415, 1360, 1330, 1295, 1255, 1225, 1190, 1140, 1090, 1070, 1040.

NMR($D_2O$, 60 Mz)$\delta_{ppm}$: 8.04 (s, 1H), 8.1–7.85 (m, 2H), 7.7–7.4 (m, 3H), 4.4–3.6 (m, 8H), 3.6–3.2 (m, 2H), 2.98 (t, J=6.9 Hz, 2H), 2.2–1.2 (m, 12H).

3-[4-(4-benzoyl-6-methylheptyl)piperazin-1-yl]-sydnonimine dihydrochloride

Melting point: 165° C. (decomp.)

IR, $\nu_{max}^{KBr}cm^{-1}$: 3400, 3020, 2940, 2700–2200, 1680, 1590, 1575, 1460, 1440, 1370, 1300, 1265, 1205, 1150, 1130, 1090, 1065, 1040, 1000.

NMR($D_2O$), 60 Mz)$\delta_{ppm}$: 9.97 (s, 2H), 8.42 (s, 1H), 8.1–7.9 (m, 2H), 7.7–7.4 (m, 3H), 4.4–2.9 (m, 11H), 2.0–1.2 (m, 7H), 0.87 (d, J=3.7 Hz, 6H).

EXAMPLE 8

| | |
|---|---|
| 3-[4-(4-benzoylbutyl)piperazin-1-yl]-sydononimine dihydrochloride | 2.0 g |
| Corn starch | 63.0 g |
| Lactose | 50.0 g |
| Talc | 9.0 g |
| Magnesium stearate | 1.0 g |
| | 125.0 g |

The above ingredients were well mixed, and formed into 125 mg tablets in a customary manner. Each of the resulting tablets contained 2.0 mg of the sydnonimine derivative as an active ingredient.

What we claim is:

1. A 3-[4-(benzoylalkyl)piperazine-1-yl]sydnonimine compound represented by the following formula (1)

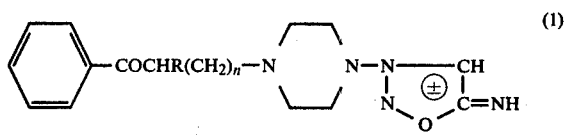

wherein R represents a hydrogen atom or an alkyl group having 1 to 8 carbon atoms, and n represents zero or an integer of 1 to 10, and its acid addition salt.

2. The compound and its acid addition salt of claim 1 wherein R in formula (1) is a hydrogen atom.

3. The compound and its acid addition salt of claim 2 wherein n in formula (1) is 3.

4. The acid addition salt of claim 1 or 3 which is a hydrochloride.

5. The compound and its acid addition salt of claim 2 wherein n in formula (1) is zero.

6. The compound and its acid addition salt of claim 2 wherein n in formula (1) is 2, 4, 5, or 7.

7. The compound and its acid addition salt of claim 1 wherein R in formula (1) is an isobutyl group.

8. A pharmaceutical composition comprising an effective amount, for exhibiting platelet aggregation inhibiting activity and vascular wall relaxing activity of a 3-[4-(benzoylalkyl)piperazin-1-yl]-sydnonimine compound represented by the following formula (1)
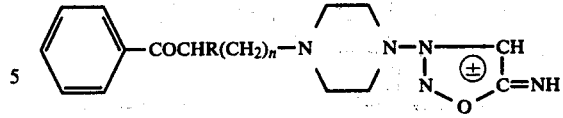
wherein R represents a hydrogen atom or an alkyl group having 1 to 8 carbon atom, and n represents a zero or an integer of 1 to 10,
or its pharmaceutically acceptable acid addition salt and a pharmaceutically acceptable diluent or carrier.
* * * * *